United States Patent [19]

Shih et al.

[11] Patent Number: 4,908,220
[45] Date of Patent: Mar. 13, 1990

[54] FEATHER-LYSATE, A HYDROLYZED FEATHER FEED INGREDIENT AND ANIMAL FEEDS CONTAINING THE SAME

[75] Inventors: Jason C. H. Shih; C. Michael Williams, both of Cary, N.C.

[73] Assignee: North Carolina State University, Raleigh, N.C.

[21] Appl. No.: 176,069

[22] Filed: Mar. 31, 1988

[51] Int. Cl.$^4$ .............................................. A23K 1/10
[52] U.S. Cl. ..................................... 426/61; 426/623; 426/630; 426/646; 426/647; 426/657; 426/807
[58] Field of Search ................. 426/61, 630, 623, 657, 426/656, 646, 647, 807; 435/272, 273; 8/94.15

[56] References Cited

U.S. PATENT DOCUMENTS

| | | | |
|---|---|---|---|
| 2,137,365 | 11/1938 | Strong et al. | 71/18 |
| 2,597,566 | 11/1949 | Chiego | 260/123.7 |
| 2,702,245 | 2/1955 | Mayer | 99/2 |
| 2,988,487 | 6/1961 | Nickerson et al. | 195/5 |
| 3,272,632 | 9/1966 | Speer | 99/2 |
| 3,578,460 | 5/1971 | Weeks et al. | 99/7 |
| 3,578,461 | 5/1971 | Weeks et al. | 99/7 |
| 3,767,799 | 7/1971 | Vertesy et al. | 424/122 |
| 3,961,096 | 6/1976 | Emanuel | 426/644 |
| 3,970,614 | 7/1976 | Goodwin | 426/556 |
| 4,151,306 | 4/1979 | Williams et al. | 426/456 |
| 4,172,073 | 10/1979 | Kadri et al. | 260/123.7 |
| 4,210,634 | 7/1980 | Jaeger | 424/101 |
| 4,210,721 | 7/1980 | Monsheimer et al. | 435/913 |
| 4,211,795 | 7/1980 | Leroy et al. | 426/2 |
| 4,220,724 | 9/1980 | Berg et al. | 435/265 |
| 4,269,865 | 5/1981 | Retrum | 426/657 |
| 4,292,328 | 9/1981 | Coulthard et al. | 426/2 |
| 4,292,334 | 9/1981 | Nishizawa et al. | 426/447 |
| 4,293,647 | 10/1981 | Monsheimer et al. | 435/69 |
| 4,294,087 | 10/1981 | Monsheimer et al. | 8/94.15 |
| 4,378,311 | 3/1983 | Retrum | 260/123.7 |
| 4,411,991 | 10/1983 | Hirakuwa et al. | 435/42 |
| 4,665,158 | 5/1987 | Armanet et al. | 530/357 |
| 4,797,362 | 1/1989 | Takauchi . | |

OTHER PUBLICATIONS

Göktan, D., "Decomposition Rates of Keratinous Material Used by Certain Microorganisms," (Abstract No. 207369b), *Microbial Biochem.* 101, 333 (1984).

Göktan, D., "The Isolation and Identification of Microorganisms that can use Some Agricultural Wastes Resistant to Enzymatic Degradation," *Mikrobiyol. Bult.* 18, 90 (1984).

Thompson, T. L. and Martin E. H., "Changes in Parmesan Cheese During Ripening: Microflora Coliforms, Enterococci, Anaerobes, Propionibacteria and Staphylococci," *Biol. Abstr.* 82, No. 4, (Abstract No. 33508) (1986).

Vallalat, T., "Production of Feed and Feed Additives by Degradation of Keratin-Containing Byproducts to Digestible Form," *Chemical Abstracts* 108, No. 5, (Abstract No. 36506g) (1988).

Williams, C. M. and Shih, J. C. H., "Microbiology of Poultry Waste Digestion and Discovery of a Feather Degrading Microorganism," *Poultry Science* 65, Supp. 1, 144 (Abstract) (1986).

Williams, C. M. and Shih, J. C. H., Manuscript Entitled "Enumeration of Some Microbial Groupsin Thermophilic Poultry Waste Digesters and Enrichment of a Feather-Degrading Culture."

Papadopoulos et al., "Effect of Different Processing Conditions of Amino Acid Digestibility of Feather Meal Determined by Chicken Assay," *Poultry Sci.* 64, 1729 (1985).

Papadopoulos, M. C., "The Effect of Enzymatic Treatment of Amino Acid Content and Nitrogen Characteristics of Feather Meal," *Animal Feed Science and Technology* 16, 151 (1986).

Williams, C. M. and Shih, J. C. H., "Isolation of a Feather-Degrading Microorganism from a Poultry Waste Digester," ASM Annular Meeting (Abstract) (1987).

Daniels, G., "The Digestion of Human Hair Keratin by Microsporum Canis," *J. Gen. Microbiol.* 8, 289 (1953).

Elmagergi, H. and Smith, R., "Influence of Growth of Streptomyces fradiae on Pepsin-HCl Digestibility and Methionine Content of Feather Meal," *Can. J. Microbiol.* 17, 1067 (1971).

Koh, W. et al., "Keratinolytic Enzymes from Aspergillus flavus and Aspergillus niger," *Bacillus. Aust. J. Biol. Sci.*, 274 (1959).

Molyneaux, G. S., "The Digestion of Wool by a Keratinolytic Bacillus," *Aust. J. Biol. Sci.* 274 (1959).

Noval, J. and Nickerson, W., "Decomposition of Native Kertain by Streptomyces Fradiae," *J. Bacteriol.* 77, 251 (1959).

"Alcalase 2.4L." Proteolytic enzyme prepared by submerged fermentation of a selected strain of Bacillus licheniformis. Novo Laboratories, Inc.

"Maxacal L. High Alkaline Protease." Gist-Brocades USA, Inc.

Dorland's Illustrated Medical Dictionary, 338 (25th ed., 1974).

J. Adler-Nissen, *Enzymic Hydrolysis of Food Proteins*, preface, contents, 20–21, 99–100, 368, 372, 373, 374, 375, 377, 387–388, 402 (1986).

Kapica, L. and Blank, F., "Growth of Candida Parapsilosis with Keratin as Sole Source of Nitrogen," *Dermatologica* 117, 433 (1958).

Kapica, L. and Blank, F., "Growth of Candida Parapsilosis with Keratin as Sole source of Nitrogen," *Dermatologica* 117, 433 (1958).

Kapica, L. and Blank, F., "Growth of Albicans on Keratin as Sole Source of Nitrogen," *Dermatologica* 115, 81 (1957).

*Primary Examiner*—R. B. Penland
*Attorney, Agent, or Firm*—Bell, Seltzer, Park & Gibson

[57] ABSTRACT

A hydrolyzed feather product, feather-lysate, is disclosed. The product comprises partially hydrolyzed feather, proteins cleaved from the partially hydrolyzed feather, peptides cleaved from the partially hydrolyzed feather, and *Bacillus licheniformis* cells. Preferably, the *B. licheniformis* cells are killed. Feather-lysate may be combined with a carbohydrate source to form an animal feed.

7 Claims, No Drawings

FEATHER-LYSATE, A HYDROLYZED FEATHER FEED INGREDIENT AND ANIMAL FEEDS CONTAINING THE SAME

FIELD OF THE INVENTION

This invention relates to animal feed ingredients generally, and particularly relates to a hydrolyzed feather feed ingredient, feather-lysate, useful as a source of dietary protein.

BACKGROUND OF THE INVENTION

Feathers are produced in large quantities by the poultry industry. These feathers provide an inexpensive source of raw material for a variety of potential uses. Among other things, there has been considerable interest in developing methods of degrading feathers so they can be used as an inexpensive source of amino acids and digestible protein in animal feed.

Processes for converting feather into animal feed which have been developed to date include both steam hydrolysis processes and combined steam hydrolysis and enzymatic processes. See, e.g., Papadopoulos, M. C., *Animal Feed Science and Technology* 16, 151 (1986); Papadopoulos, M. C. et al., *Poultry Science* 64, 1729 (1985); Alderibigde, A. O. and D. Church, *J. Anim. Sci.*, 1198 (1983); Thomas and Beeson, *J. Anim. Sci.* 45, 819 (1977); Morris and Balloun, *Poultry Sci.* 52, 858 (1973); Moran et al., *Poultry Sci.* 46, 456 (1967); Davis et al., Processing of poultry by-products and their utilization in feeds. Part I. *USDA Util. Res. Rep.* no. 3, Washington, DC (1961). Disadvantages of these procedures, such as the degradation of heat sensitive amino acids by steam processes and the relatively low digestibility of the resulting products, have lead to continued interest in economical new feather degradation procedures which do not require a harsh steam treatment.

Accordingly, an object of the present invention is to provide a process for hydrolyzing keratinaceous material which does not depend upon steam hydrolysis.

An additional object is to provide a process for converting keratinaceous material into amino acids at high yields of the amino acids.

A further object of this invention is to provide a hydrolyzed feather product useful as a feed ingredient which is highly digestible and provides a good quality source of dietary protein and amino acids.

A still further object of the present invention is to provide an economical animal feed which employs a hydrolyzed feather product as a dietary amino acid source.

The foregoing and other objects and aspects of the present invention are explained in detail in the Summary, Detailed Description, and Examples sections below.

SUMMARY OF THE INVENTION

A first aspect of the present invention is a method of degrading keratinaceous material. The method comprises the steps of combining keratinaceous material with *Bacillus licheniformis* to form a fermentation media, and then fermenting the media for a time sufficient to degrade the material. In addition to degrading keratinaceous material, the method of the present invention can be used to produce amino acids. In this case, a fermentation media produced as described above is fermented for a time sufficient to produce free amino acids therefrom, and the free amino acids are recovered from the media.

The method of the present invention can also be used to produce a hydrolyzed feather product. In this latter case, a fermentation media produced as described above, with feather as the keratinaceous material, is fermented for a time sufficient to increase the digestibility of the media (e.g., by enriching the concentration of digestible proteins and peptides therein). Preferably, the bacteria in the media are then killed to form a hydrolyzed feather product useful as a feed ingredient (i.e, the media with the bacteria are treated to kill the bacteria).

When the method of the present invention is used to produce free amino acids or a hydrolyzed feather product, the fermentation step is preferably an anaerobic fermentation step. Under anaerobic conditions, *B. licheniformis* does not actively grow. Hence, the utilization of amino acids by *B. licheniformis* is decreased and free amino acid production, or enrichment, is increased. In addition, prior to the step of combining the feathers with *B. licheniformis*, *B. licheniformis* is preferably first grown under aerobic conditions (preferably in a liquid culture) to obtain enriched quantities of active bacteria. These procedures, as explained in detail below, provide an efficient and cost-effective way to degrade keratinaceous material and to utilize feather.

A second aspect of the present invention is a pure culture of the keratinaceous material-degrading microorganism having the identifying characteristics of *Bacillus licheniformis* PWD-1, ATCC No. 53757. *B. licheniformis* PWD-1 is the preferred microorganism for carrying out the methods described above.

A third aspect of the present invention is a hydrolyzed feather product, which may be produced by the method described above. This product comprises partially hydrolyzed feather, proteins cleaved from the partially hydrolyzed feather, peptides cleaved from the partially hydrolyzed feather, and *B. licheniformis* cells (preferably killed *B. licheniformis* cells). This hydrolyzed feather product may be combined with a carbohydrate source and, preferably, minerals and vitamins, to form an animal feed. A second, supplementary protein source may optionally be included in the feed.

Additional aspects of the present invention are discussed below.

DETAILED DESCRIPTION OF THE INVENTION

The present invention can be carried out with all types of keratinaceous material, including hair, hooves, and feather. Feather is preferred. Any type of feather may be employed, including chicken, turkey, and duck feather. Chicken feather is preferred, and is the material recited in the text which follows. However, the teaching of this text is applicable to the degradation and utilization of all keratinaceous materials.

Prior to combining feather with *B. licheniformis* to form a fermentation medium, the feather should be sterilized to kill bacteria naturally present on the feather which might otherwise disrupt the fermentation process. This sterilization step may be carried out by any means, including fumigation by contacting feather to formalin or ethylene oxide gas, by contacting feather to steam under pressure, or by combinations of the same. We have found that, by contacting feather to steam under pressure, even for a time insufficient to sterilize the feather, subsequent bacterial degradation of the feather is substantially improved. Accordingly, sterilization steps in the present invention preferably include a step of contacting the feather to steam for a time and at a temperature sufficient to facilitate the subsequent bacterial hydrolysis thereof, even if this steam treatment step does not accomplish a complete sterilization of the feather. We have found that contacting feather to steam under pressure, in an enclosed chamber, at 125 degrees Centigrade for a time as brief as 2 minutes is sufficient to substantially enhance the subsequent fermentation hydrolysis thereof. If sterilization of feather is carried out solely by steam, the feather should be contacted to steam under pressure at 125 degrees Centigrade for at least 15 minutes (a 15-20 minute treatment at this temperature being, by definition, an autoclaving step). The time and temperature of steam treatment should be less than those employed in commercial steam hydrolysis processes, which employ treatment times of 35 minutes or more at steam pressures of about 35 p.s.i. or more.

Prior to fermentaton, *B. licheniformis* can be grown aerobically in any suitable liquid growth medium (preferably a feather-based liquid growth medium). The bacteria is preferably grown at a temperature of from about 45 to about 55 degrees centigrade. After a sufficient quantity of the bacteria is grown (preferably about $10^8$ colony forming units per milliliter), the liquid growth medium is combined with feather in any suitable fermentation vessel. Preferably, the liquid growth medium and feather are combined at a high proportion of feather, so that the fermentation is a semi-solid fermentation. A preferred fermentation media comprises, by weight, at least about 1 part of dry feather per 4 parts of liquid growth medium, or more preferably about 1 part of dry feather per 2 parts of liquid growth medium.

Carbohydrate sources used to produce an animal feed according to the present invention include, for example, corn, oats, barley, sorghum, or combinations of the same. These grains are preferably ground into a meal for use in the animal feed. Supplementary protein sources include, for example, soy meal, fish meal, blood meal, poultry by-product (ground poultry offal), meat meal, and combinations of the same. An animal feed is comprised of from about 13% to about 25% by weight of protein from all protein sources (both hydrolyzed feather and supplemental). The hydrolyzed feather product may be the sole protein source, but is preferably from about 2% to about 15% by weight of the feed. Other nutrients in small amounts, such as vitamins, minerals, antibiotics, and other substances or compounds may be included in the feed as required.

*Bacillus licheniformis* strain PWD-1 was deposited with the American Type Culture Collection in accordance with the Budapest Treaty on Mar. 23, 1988, and has been assigned ATCC Accession No. 53757.

PWD-1 has been found to be a gram positive (but gram variable) bacteria. It is a straight rod-shaped bacteria, the rods being from about 2.1 to about 3.0 microns long and from about 0.5 to about 1.0 microns wide, with the ends of the rods being rounded. Bacterial cells are found both singly and in chains. One subterminal endospore is formed per cell, the endospore being centrally located and cylindrical or oval in shape.

PWD-1 forms opaque, entire (mucoid) colonies which are erose and irregular in shape. Low convex, high convex (mucoid) and flat colonies are seen. Colonies are seen to disassociate. The colonies are observed as glistening (mucoid) dull, dry, smooth (mucoid) and rough, with an insoluable brown pigment present. Cells are motile (flagella being present) and peritrichous.

PWD-1 grows at temperatures of from about 20° C. to about 55° C., with trace growth being present at 60° C. In our hands, the bacteria is thermophilic, growing best at temperatures of from 45° to 50° C. Others have reported an optimum growth range of between 21 and 30 degrees Centigrade. Experiments are under way to examine the effects of different growth media on optimum growth temperature.

PWD-1 produces acid, but not gas, from L-arabinose, D-xylose (weakly), D-glucose, lactose (weakly), sucrose, and D-mannitol. It can utilize both citrate and propionate as a carbon source. PWD-1 hydrolyzes polysaccharide, starch and casein, but not hippurate. PWD-1 liquifies gelatin. It reduces, but does not reoxidize, methylene blue. It reduces nitrate to nitrite, but it does not reduce nitrite.

PWD-1 is Voges Proskauer (5198) positive, Voges Proskauer (5198 fil) positive, and Voges Proskauer (5331) positive. It decomposes hydrogen peroxide but not tyrosine, is negative for indole, and is positive for dihydroxyacetone. PWD-1 is negative in the Litmus milk acid test, negative in the Litmus milk coaulation test, and negative in the Litmus milk alkaline test, but is positive in both the litmus milk peptonization and litmus milk reduction tests.

PWD-1 grows at a pH of 5.7 and at a pH of 6.0. It shows a pH VP5198 of 8.0 or more. The optimum pH in nutrient broth is 7.0 to 7.5. It is aerobic and facultative. It does not grow in 0.02% azide. It generates gas from sealed nitrate and grows in sealed glucose. It is negative for lecithinase.

The present invention is explained further in the following examples. These examples are provided for illustrative purposes only, and are not to be taken as limiting.

EXAMPLE 1

Comparison of Amino Acid Production By Aerobic and Anaerobic Fermentations

*Bacillus licheniformis* PWD-1 was grown in two batches of a sterile aqueous medium containing feather as the sole source of carbon and energy. Each liter of medium contained 0.5 grams of $NH_4Cl$, 0.5 grams of NaCl, 0.3 grams of $K_2HPO_4$, 0.4 grams of $KH_2PO_4$, 0.24 grams of $MgCl_2.6H_2O$, 1.0 grams of hammermilled feather (a coarsely chopped feather) and 0.1 grams of yeast extract. The media were adjusted to a pH of 7.5. Each culture was incubated at 50 degrees Centigrade, one being grown under aerobic conditions and the other being grown under anaerobic conditions. The quantity of amino acids found in the media at day zero (prior to inocculation) and after five days of incubation under both aerobic and anaerobic conditions, is shown in Table 1 below.

TABLE 1

Free amino acid concentrations in the growth medium of feather degrading microorganisms under aerobic and anaerobic conditions.

| Amino Acid (mg/l) | Day 0 | Day 5 Aerobic | Day 5 Anaerobic |
|---|---|---|---|
| ASP (N) | 0.00 | 0.00 | 3.40 |
| THR | 0.78 | 0.90 | 9.00 |
| SER | 0.83 | 1.10 | 7.60 |
| GLU (N) | 0.00 | 1.70 | 11.80 |
| GLY | 1.61 | 0.50 | 6.60 |
| ALA | 1.35 | 1.10 | 14.50 |
| CYS | 0.11 | 3.00 | 10.20 |
| VAL | 0.36 | 2.10 | 17.10 |

TABLE 1-continued

Free amino acid concentrations in the growth medium of feather degrading microorganisms under aerobic and anaerobic conditions.

| Amino Acid (mg/l) | Day 0 | Day 5 Aerobic | Day 5 Anaerobic |
|---|---|---|---|
| MET | 0.00 | 1.90 | 4.60 |
| ILE | 0.19 | 1.70 | 20.70 |
| LEU | 0.91 | 2.10 | 32.60 |
| TYR | 0.00 | 0.00 | 6.30 |
| PHE | 0.00 | 3.30 | 22.40 |
| ORN | 0.00 | 0.70 | 7.50 |
| LYS | 0.99 | 3.10 | 6.80 |
| HIS | 0.22 | 0.00 | 2.70 |
| ARG | 1.05 | 1.00 | 11.20 |
| TOTAL | 8.40 | 24.20 | 195.00 |

These data show that the total production of amino acids was approximately 800% greater under anaerobic conditions than under aerobic conditions.

EXAMPLE 2

Amino Acid Yields in Semi-Solid Fermentations

PWD-1 was grown in a liquid media like that described in Example 1 (except that 10.0 grams of hammer milled feather per liter was used instead of 1.0 gram/liter) for 5 days at 50 degrees Centigrade under aerobic conditions to reach $10^8$ CFU per milliliter. An additional quantity of hammer milled feathers was autoclaved with steam at 125 degrees Centigrade (16 p.s.i.) for 15 minutes. The feathers were mixed with the growth medium at a proportion of 250 grams feather per liter of growth medium in a fermentation vessel to form a fermentation medium, and the fermentation medium was flushed with nitrogen. The fermentation medium was then incubated anaerobically for five days at 50 degrees Centigrade with periodic agitation. The same procedure was carried out on a separate occasion, except that the fermentation step was carried out aerobically. These procedures were duplicated for both conditions. The amino acid concentrations in the liquid phase of all the fermentation media were measured on day five of fermentation, these data being given in Table 2 below.

TABLE 2

Total free amino acid concentrations (g/l) in the liquid phase of the semi-solid phase fermentations

| Fermentation | Anaerobic | Aerobic |
|---|---|---|
| 1 | 14.7 | 1.7 |
| 2 | 12.4 | 1.9 |

Note that, under anaerobic conditions, free amino acids are produced in quantities in excess of 10 grams/liter by semi-solid phase fermentations.

EXAMPLE 3

Production of a Hydrolyzed Feather Meal Food Product

After five days of anaerobic fermentation, a semi-solid fermentation medium like that described in Example 2 above was autoclaved with steam at 125 degrees Centigrade for 15 minutes, then dried at 60 degrees Centigrade for 48 hours, and then milled through a one millimeter mesh. The resulting product was a brown powder comprised of partially hydrolyzed feather, short peptides, amino acids, and killed *Bacillus licheniformis* bacterial cells. This product is useful, among other things, as a dietary source of protein for growing chickens, as shown in Example 4 below.

EXAMPLE 4

Animal Feeds Incorporating Bacillus Licheniformis Hydrolyzed Feather

One hundred and twenty-eight chicks were divided into four equal groups, 4×8 in each group. Each group was raised on a different diet: group (a) was raised on corn-soy feed/20% protein; group (b) was raised on corn-soy feed/15% protein; group (c) was raised on corn-soy feed/15% protein plus 5% unhydrolyzed hammer-milled feather; group (d) was raised on corn-soy feed/15% protein plus 5% protein from *Bacillus licheniformis* hydrolyzed feather produced in accordance with the procedure described in Example 3 above. All birds were weighed at three weeks of age and the weights for each group averaged. These averages are shown in Table 3 below.

TABLE 3

Ability of growing chickens to utilize feather-lysate as a dietary protein source.

| Diet | Mean Body Weight (grams) M ± SEM |
|---|---|
| Standard corn-soy, 20% protein | 554.7 ± 8.5 |
| Standard corn-soy, 15% protein | 503.9 ± 8.3 |
| Corn-soy, 15% protein + 5% protein from untreated feathers | 458.8 ± 7.1 |
| Corn-soy, 15% protein + 5% protein from feather-lysate | 525.6 ± 8.9 |

These data show that *Bacillus licheniformis* hydrolyzed feather can be used as an inexpensive source of dietary protein in animal feed.

The foregoing examples are provided to illustrate the present invention, and are not to be taken as restrictive thereof. The scope of the invention is defined by the following claims, with equivalents of the claims to be included therein.

That which is claimed is:

1. A hydrolyzed feather animal feed supplement consisting essentially of partially hydrolyzed feather, proteins cleaved from said partially hydrolyzed feather, peptides cleaved from said partially hydrolyzed feather, and *Bacillus licheniformis* PWD-1 (ATCC No. 53757) cells, said feather hydrolyzed to an extent sufficient to increase the digestability thereof.

2. A hydrolyzed feather animal feed supplement as claimed in claim 1, wherein said *Bacillus licheniformis* PWD-1 cells are killed *Bacillus licheniformis* PWD-1 cells.

3. A hydrolyzed feather animal feed supplement as claimed in claim 1 produced by fermenting said feather with living *Bacillus licheniformis* PWD-1 bacteria.

4. An animal feed comprising a carbohydrate source and a first protein source, said first protein source consisting essentially of partially hydrolyzed feather, proteins cleaved from said partially hydrolyzed feather, peptides cleaved from said partially hydrolzed feather, and killed *Bacillus licheniformis* PWD-1 (ATCC No. 53757) cells, said feather hydrolyzed to an extent sufficient to increase the digestability thereof.

5. An animal feed as claimed in claim 4, wherein said carbohydrate source is selected from the group consisting of corn meal, oat meal, barley meal, sorghum meal, and combinations of the same.

6. An animal feed as claimed in claim 4, further comprising a supplemental second protein source.

7. An animal feed as claimed in claim 6, wherein said supplemental protein source is selected from the group consisting of soy meal, fish meal, blood meal, ground poultry offal, meat meal, and combinations of the same.

* * * * *